United States Patent [19]
Segel et al.

[11] Patent Number: 5,967,789
[45] Date of Patent: Oct. 19, 1999

[54] METHOD AND SYSTEM FOR STOPPING OR MODIFYING UNDESIRABLE HEALTH-RELATED BEHAVIOR HABITS OR MAINTAINING DESIRABLE HEALTH-RELATED BEHAVIOR HABITS

[75] Inventors: Joseph M. Segel, Bryn Mawr, Pa.; Michael H. Samuelson, Saline, Mich.

[73] Assignee: Smoke Stoppers International, Inc., Bryn Mawr, Pa.

[21] Appl. No.: 09/126,410

[22] Filed: Jul. 30, 1998

[51] Int. Cl.⁶ .............................. G09B 19/00; A24F 47/00
[52] U.S. Cl. ........................... 434/236; 434/238; 131/270
[58] Field of Search .................................. 434/236, 237, 434/238; 40/107; 131/270; 283/2, 3, 4

[56] References Cited

U.S. PATENT DOCUMENTS

| | | |
|---|---|---|
| 3,737,863 | 6/1973 | Rowland et al. . |
| 4,853,854 | 8/1989 | Behar et al. . |
| 4,877,041 | 10/1989 | Barnhouse . |
| 4,951,197 | 8/1990 | Mellinger . |
| 4,976,622 | 12/1990 | Clark . |
| 5,016,917 | 5/1991 | Dubner et al. . |
| 5,090,733 | 2/1992 | Bussiere . |
| 5,135,260 | 8/1992 | Irlik et al. . |
| 5,207,580 | 5/1993 | Strecher . |
| 5,431,450 | 7/1995 | Coleman . |
| 5,443,288 | 8/1995 | Miles . |
| 5,711,671 | 1/1998 | Geeslin et al. . |
| 5,879,163 | 3/1999 | Brown et al. ............................ 434/236 |

OTHER PUBLICATIONS

"Quitters Countdown: Preparing to Stop"; and.
"NICODERM $_{CQ}$ Committed Quitters Calendar and Smoking Cessation Services".

*Primary Examiner*—Robert A. Hafer
*Assistant Examiner*—John Edmund Rovnak
*Attorney, Agent, or Firm*—Caesar, Rivise, Bernstein, Cohen & Pokotilow, Ltd.

[57] ABSTRACT

A system and method of use to help a person to stop or modify an adverse habitual health-related behavior, e.g., smoking, weight control, stress management, etc., by following a calculated regimen to commence on a day to be selected by the person. The system comprises a computer and a series of customized visually perceptible messages establishing a customized regimen to aid the person to stop or modify the adverse habitual health-related behavior. The computer is arranged to receive personal information about the person and which is relevant to the behavior and makes use of expert system software to provide the customized messages in response thereto. The customized messages are in the form of a daily sequence measured relative to day selected by the person for the regimen to begin. Each of the messages is arranged to be read by the person in sequence on a daily basis and includes respective numerical indicia representing the number of days from the selected day to the day of said message. The messages are provided to the person in various ways, e.g., delivered to the person on a daily basis by means of some electronic communication medium, such as the Internet, e-mail, facsimile, etc., where they are printed out by the person. Alternatively, the cards or sheets may be generated by the system and provided to the person in hard copy form. The messages produced by the system may be updated and modified based upon information provided to the system by the person. Moreover, messages may be provided by the system to a support person to aid the person wishing to change his/her health-related behavior.

30 Claims, 5 Drawing Sheets

Fig. 4

FRONT

| *John Doe's Quit Smoking Plan* | PERSONAL PROFILE |

Here is your custom-tailored *Quit Smoking Plan* from Smoke Stoppers – developed exclusively for you based upon the following information that you provided.

John Doe's Personal Profile

Your age ..................................................................53
Your sex ...............................................................*Male*
Other smokers in your household.......................*1*
Average number of cigarettes you smoke per day..........*20*
Number of times you have tried to quit..........*3*
Longest period you have not smoked..............*3.5 months*
Your last quit attempt: ...........................*June 1997*
Nicotine products you have tried: ..............*Patch; Gum*
Do you smoke within 30 minutes of getting up?..........*Yes*
Why you smoke:
  *Pleasure; stress release; self-reward*
Why you want to quit:
  *Health concerns; pressure from family*
What you believe are your barriers to quitting:
  *Fear of gaining weight; lack of willpower*
What you feel are your smoking "triggers:"
  *After meal ritual; driving; stressful situations;alcohol*
How you appraise your confidence level:
  *Somewhat confident*

BACK

Welcome!

This is your personal *Quit Smoking Plan*. It won't work as well for anybody else because it was designed *exclusively* for you, based on your personal profile.

There are 21 numbered cards in this kit. – one card per day for the next three weeks. Each morning, take out that day's card and read it thoroughly, front and back. Follow each card's instructions. If you wish, you can carry your daily card with you throughout the day as a ready reminder of the plan for that day.

You may be feeling anxious or nervous. This is perfectly natural. You are starting on an important journey. At times, especially in the beginning, it will be difficult. Take comfort in the fact that you will complete this journey because you have *an action plan*...a "roadmap" prepared especially for you, which will help you achieve a healthier, happier lifestyle.

Follow your plan. Studies show that people who closely follow their personal plan have the best chance of success. Don't cut corners. Even if some of the suggestions and exercises may seem unnecessary, they are based on years of research – and they really do work! It is well worth the effort to become a comfortable nonsmoker for the rest of your life..

Fig. 5

FRONT

*John Doe's Quit Smoking Plan* | DAY 1

This is your QUIT DAY – Congratulations!

Because you've tried to stop smoking several times in the past, you know how tough the "quit day" can be. But you now have a plan, and by following the instructions on the front and back of this card, you will get through it!

You told us that "gaining weight" is one of your major concerns about quitting smoking. Therefore, it's vitally important that you avoid fatty foods and foods with high sugar content. Stock-up on things such as sugarless candy and gum, carrot and celery sticks, fresh fruits and vegetables, whole grain breads and low-sugar fruit juices. At least for the next few weeks, make a commitment to eating healthy – especially when it comes to snacks.

"Lack of willpower" is another of your concerns. Quitting smoking does require at least a little willpower – but more importantly it requires knowing what to expect and being prepared to cope. Willpower alone doesn't normally work because you can't break a habit simply by denying it. Breaking a habit is a mostly mechanical process that requires a plan. And this plan should work for YOU. Just follow it closely.

BACK

Rules for Becoming a Comfortable Nonsmoker
DAY 1

1. <u>Get rid of all smoking materials.</u> Destroy all cigarettes and remove all ashtrays, lighters and matches from your home, workplace and car.
2. <u>Vary your daily routines</u> – they are what lock you into your smoking habit. Listen to a different radio station. Watch different TV programs. Don't sit in your favorite easy chair. Avoid people who smoke. *Change the routine habits that trigger your urges to smoke.*
3. <u>After meals,</u> don't linger at the table. Brush your teeth and rinse with mouthwash. Take a brisk walk and reflect on your decision to stop smoking.
4. <u>Get your full requirement of sleep.</u>
5. <u>Shower or bath both in the AM and PM</u> to reinforce your commitment to "stay clean" of cigarettes.
6. <u>Try to exercise</u> for at least 15-30 minutes per day. Walking, jogging, swimming, bike riding, etc. are all good exercises. *Stay active.*
7. <u>Keep busy.</u> Go to a movie. Visit a nonsmoking friend. Clean out the closet. Read a good book.
8. <u>Eat healthy.</u> Avoid sweets, and NO ALCOHOL!
9. <u>Be prepared for smoking urges.</u> Practice breathing deeply and the "ex-smoker's ritual."

Remember, the urge to smoke normally lasts for only a couple of __minutes__ – and it will go away whether you smoke or not.

METHOD AND SYSTEM FOR STOPPING OR MODIFYING UNDESIRABLE HEALTH-RELATED BEHAVIOR HABITS OR MAINTAINING DESIRABLE HEALTH-RELATED BEHAVIOR HABITS

BACKGROUND OF THE INVENTION

This invention relates generally to systems and methods for facilitating the self-modification of undesirable health-related behavior in human beings and for facilitating the maintenance of desirable health-related behavior.

Various methodologies and/or systems have been proposed and are publically available to help persons change an unhealthy or otherwise undesirable habitual health-related behavior. The training of persons to help them cease smoking is one such common application. For example, one approach to training persons to break their smoking habit was a plan or regimen provided by National Health Promotions, Inc. under the Service Mark SMOKE STOPPERS®. That plan made use of a bound, multi-page workbook entitled "Quitter's Countdown: Preparing to Stop," Copyright 1991, by the National Center for Health Promotion. The workbook included a multi-page questionnaire to be filled out by an individual desiring to quit smoking. Following the questionnaire portion in the workbook was a sequence of pages establishing the regimen of the non-smoking plan to be followed by the individual. In particular, those succeeding pages of the workbook included instructions for each successive day of the plan, e.g., instructions for "Day One," "Day Two," etc. These daily instructions were spread out over plural pages in the workbook and included text, charts, diagrams, etc.

Other workbooks have been used as part of smoking cessation plans. For example, as part of the commercialization of its Nicoderm® nicotine replacement product, SmithKline Beecham provides a workbook or booklet in the form of a calendar having daily instructions which are specifically tailored for the individual based on information provided by the individual. The calendar includes weekly dated pages. In particular, each weekly page bears indicia identifying the date for each of the days of that week, e.g., May $20^{th}$ to May $26^{th}$, as well as indicia counting the number of days the individual has been on the plan. For example, if the individual starts the plan on May $20^{th}$ the calendar entry for May $20^{th}$ has indicia saying "Day One," whereas the calendar entry for May $21^{st}$ bears the indicia "Day Two," etc.

While the workbook or calendar approach for providing daily instructions to achieve health-related behavior modification has considerable merit, it is believed to suffer from several drawbacks. One of the most significant drawbacks is that the multi-page format of the materials for each day of the plan tends to overwhelm the individual with excessive information. Moreover, the fact that the workbook is bound and includes all of the materials provided at one time, enables the individual to prematurely view latter stage instructions, which could tend to distract the individual. Further still, if the daily pages include the calendar date, so that the plan is tied to any particular date (e.g., the first day of the plan is June 6th), it is susceptible to deviation by the individual as will be discussed later.

U.S. Pat. No. 5,207,580 (Strecher) discloses a health-related behavior change and adherence aid system which overcomes various disadvantages of the prior art. The disclosed embodiments of that system are particularly directed to helping a person stop smoking permanently and utilizes the technique of "computer tailoring" to derive a particular regimen to be followed by the individual wishing to stop smoking. To that end, health risk and psychological information is gathered from the individual. That information comprises demographic information relevant to the health risk, history and patterns of the existing health-related behavior, motives to change that behavior, a specific behavior change goal, specific dates for beginning phases of the health-related behavior change process, and barriers to changing the health-related behavior. This data is provided into a computer system for processing to develop a specific or "tailored" plan best suited to that individual to maximize his/her chance of success. Thus, the computer makes use of an algorithm to process the data to produce a customized plan or regimen to be followed. To facilitate the plan the person is provided with a calendar defining the plan and instructions and recommendations for the individual to follow. The calendar is provided to the individual either in the form of a single monthly calendar sheet, i.e., a sheet with spaces for each day of the month, or series of date book pages. In either case the calendar includes spaces containing specific instructions and advice for the individual to follow. Moreover, and quite significantly, each of the days of the calendar are "dated." That is, they bear indicia with the specific calendar date of that day. For example, as shown in FIGS. 1 and 5 the June calendar is in the form of a grid showing each of the days from June $1^{st}$ to June $30^{th}$ in its respective space. Each space for each day includes indicia identifying the day, e.g., "Wednesday" along with the date, e.g., June $3^{rd}$. In the exemplary embodiment described and shown in FIG. 5, a specific day is chosen for the individual to begin to stop smoking. That is identified as the "quit" day. In this exemplary embodiment the quit day is Tuesday, June $9^{th}$. The monthly calendar sheet entry for June $9^{th}$ includes the printed indicia "QUIT DAY GET RID OF ALL CIGARETTES." Other days of the month also bear a tailored message, e.g., Saturday, June $15^{th}$ bears the indicia "STAYING OFF: AVOIDING WEIGHT GAIN, STRESS," Monday, June $15^{th}$ bears the indicia "STAYING OFF: NICOTINE THERAPY CHECKUP," etc. In a second, but not illustrated, embodiment the information contained in the spaces of the calendar are stated to be "placed in the spaces for the appropriate diary format, for example, a diary having all or part of a month, week or day per page." Like the first embodiment, each page is "dated," that is, it bears indicia identifying the particular calendar date, e.g., Tuesday, June $9^{th}$.

While the system and methodology of the Strecher patent are generally suitable for their intended purposes, they still leave something to be desired from the standpoint of efficiency and efficacy. In particular, by relying on "dated pages," wherein the particular instructions of the regimen are tied to a specific calendar date (e.g., the quit date being June $9^{th}$), should the individual miss that date or any other and thus get out of synchronism with the plan, he/she may wind up skipping a day or days to get back in synchronism with the regimen. This deviation from the plan may result in its failure. Moreover, by presenting the information in the form of a monthly calendar, like shown in FIGS. 1 and 5, with all the information for each day of the month being perceptible at one time, the individual may be overwhelmed by the information and/or may become distracted by prematurely reading latter day instructions. Thus, it is believed that the system of the Strecher patent provides too much information on the one hand, while also providing too little information on the other. With regard to the latter, it can be seen that the amount of information provided for a specific day is rather limited by the inherent size of the monthly calendar sheet and the particular daily spaces for the daily instructions.

Other prior art methodologies or systems exist for providing information to individuals wishing to modify a habit or some undesirable health-related behavior are found in the following U.S. Pat. No. : 4,951,197 (Mellinger); U.S. Pat. No. 4,853,854 (Behar et al.). Regimen calendars have also been proposed in the patent literature, e.g., U.S. Pat. No. 5,016,917 (Dubner) and U.S. Pat. No. 5,090,733 (Busiere).

Notwithstanding the foregoing prior art, a need exists for an effective system and methodology to be used by persons desiring to change an undesirable health-related behavior or to maintain a desirable health-related behavior.

OBJECTS OF THE INVENTION

It is a general object of this invention to provide a system and method which address that need.

It is another object of this invention to provide a system and method which overcomes the disadvantages of the prior art.

It is a further the object of this invention to provide a methodology and system for establishing a regimen to enable a person to cease an undesirable health-related behavior or to maintain a desirable health-related behavior in accordance with a series of specific behavioral change messages which are provided in a daily sequence measured relative to a day that the individual wishes to commence the regimen, and which is not tied to any particular calendar date.

It is a further object of this invention to provide a tailored regimen for altering an undesirable health-related behavior or maintaining a desirable health-related behavior based on personal information provided by the individual, and which plan is provided via sequential daily messages which are not dated, but which include indicia indicating the relative day of the plan, i.e., the number of days from the day on which the plan commenced.

It is a further object of this invention to provide a system and method for providing information to an individual desiring to change an undesirable health-related behavior or to adhere to a health-related desirable behavior in a manner which avoids overwhelming the individual with excessive information.

It is a further object of this invention to provide a system and method for providing information to an individual desiring to change an undesirable health-related behavior or to adhere to a desirable health-related behavior in a manner to avoid distracting the individual with prematurely disclosed, latter stage instructions.

It is still a further object of this invention to provide a series of personalized instructions in the form of daily messages which are generated by an expert system in response to information provided by an individual to produce narrative instructions to aid the individual to change an undesirable health-related behavior to adhere to a desirable health-related behavior.

It is still a further object of this invention to provide a system and methodology of providing messages in the form of a series of cards or sheets provided to an individual in a daily sequence on daily basis.

It is yet another object of this invention to provide personalized instructions for an individual to modify an undesirable health-related behavior or to maintain a desirable health-related behavior wherein the instructions are communicated as daily messages through electronic telecommunication means.

SUMMARY OF THE INVENTION

These and other objects of the subject invention are achieved by providing a system and method of use to help a person to stop an undesirable habitual health-related behavior or maintain a desirable health-related behavior by following a calculated regimen to commence on a day to be selected by the person.

The system comprises a computer and a series of customized visually perceptible messages generated by it. The messages establish a customized regimen to aid the individual to stop the undesirable health-related behavior or to maintain the desirable health-related behavior. The computer is arranged for receipt of personal data collected from the individual based on his/her answers to a questionnaire. The computer processes that personal data, e.g., makes use of expert system software, to develop and provide the series of customized messages.

The messages are provided to the individual in a daily sequence, starting on the day selected by the person for the regimen to begin (the "selected day") and on a predetermined number of consecutive days thereafter. Each message is arranged to be visually perceived by the person on a daily basis. Each message includes respective numerical indicia representing the number of days from the day selected by the individual to start the plan to the day of the message (e.g., "DAY 1" constitutes the start of the plan, "DAY 5" constitutes the fifth day of the plan, "DAY 8" constitutes the eighth day of the plan, etc.).

Each of the series of customized messages is arranged so that each is seen on the specific day of the plan, e.g., the fifth day or "Day 5," to deter the person from seeing more than a single day's message at a time. The messages are preferably delivered to the person on a daily basis, but may be provided all at once. In either case they are delivered by any suitable means, e.g., in hard copy or by an electronic communication medium, such as the Internet, e-mail, facsimile, etc.

DESCRIPTION OF THE DRAWING

Other objects and many attendant features of this invention will become readily appreciated as the same becomes better understood by reference to the following detailed description when considered in connection with the accompanying drawing wherein:

FIG. 4 is an enlarged plan view of the front and rear sides of an exemplary introductory instruction card or sheet produced in accordance with this invention for use by a person desiring to quit smoking; and FIG. 5 is an enlarged plan view of front and rear sides of an exemplary "Day 1"(the first day of the plan) instruction card or sheet produced in accordance with this invention for use by a person desiring to quit smoking.

DETAILED DESCRIPTION OF THE PREFERRED EMBODIMENTS

Figure 1:
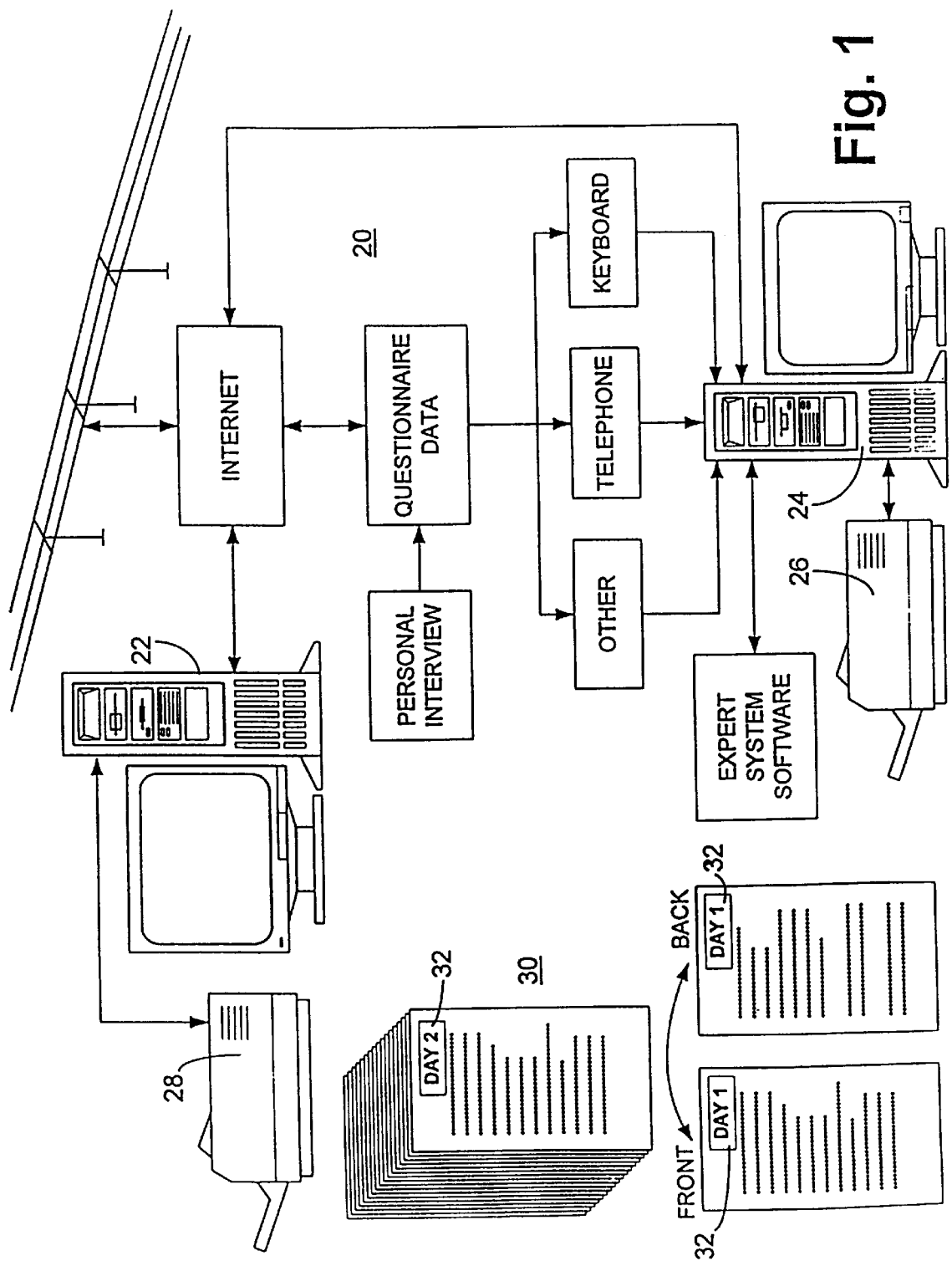
FIG. 1 is a generalized combination block and schematic diagram showing a system of the subject invention.

Referring now to the drawing where like reference numerals refer to like parts there is shown at 20 in FIG. 1 a system constructed in accordance with this invention to produce a specific customized or tailored plan to an individual wishing to modify, e.g., stop, an undesirable health-related behavior or to maintain a desirable health-related behavior. The system is particularly suited for facilitating smoking cessation, weight reduction, stress control, or other health-related behaviors. To achieve that end the system produces and provides a series of customized daily messages 30 to be followed by the individual for whom the plan is designed. The plan is custom developed for the individual in accordance with personal information provided by the individual.

It should be pointed out at this juncture that the system shown in FIG. 1 is generalized since it can be used for any type of health-related behavior modification/maintenance based on information provided by the individual. Thus, FIG. 1 shows various ways that personal information data about an individual for whom the plan is to be developed is provided into the system, as well as various ways the data can be communicated to a system computer for processing and various ways the plan's messages 30 can be delivered to the individual. In short, the system 20 shown in FIG. 1 is merely exemplary and other systems can be constructed in accordance with this invention.

Figure 2:
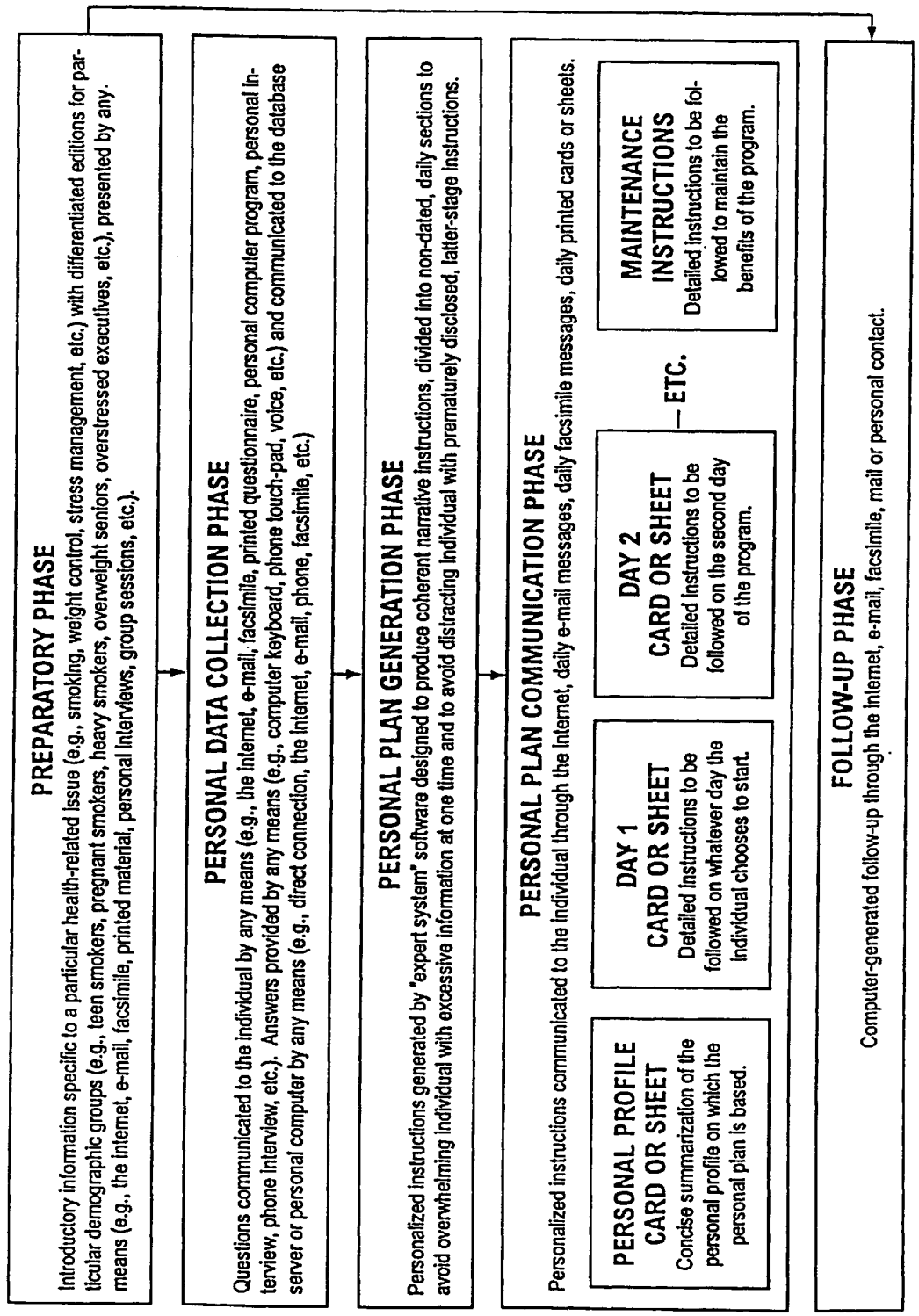
FIG. 2 is a flow chart showing the methodology employed by the subject invention for various applications, e.g., to enable a person to quit smoking, control his/her weight, manage stress, etc.

In accordance with one preferred methodology of this invention, before the customized plan is developed a "Preparatory Phase" is conducted. The Preparatory Phase is shown in the block diagram of FIG. 2 and basically consists of providing the potential user of the plan introductory information which is specific to the particular health-related behavior to be altered or maintained. For example, if the health-related behavior is smoking, the individual is provided with specific introductory information relating to smoking. Preferably, that information is differentiated to the individual's particular situation, e.g., teen smokers, pregnant smokers, heavy smokers, etc. This preparatory information can be provided to the individual by any suitable means, e.g., a personal interview or a group session, mail, the Internet, e-mail and facsimile.

After the Preparatory Phase has been completed, the "Personal Collection Phase" of the plan is undertaken. In that phase questions are communicated to the individual to gather personal information from him/her to customize or tailor the plan so that it has its greatest chance of success. The questions for the individual may be of the type utilized in the aforementioned Strecher patent or any others deemed suitable. Those questions can be communicated to the individual by any suitable means, such as a personal interview, a telephonic interview, facsimile, or a printed questionnaire. If the individual has his/her own computer system 22 (FIG. 1), the questionnaire may be provided via e-mail or an Internet web site. Alternatively, the individual may be provided with a personal computer program disk or CD to run on his/her computer to provide the questions. If the person has a facsimile machine the questions can be provided via that machine. The individual's answers to the questions of the questionnaire may be provided into the system 20 via any suitable means, e.g., personal interview, telephonic interview, access to an Internet web site, e-mail, facsimile or return of an answered printed questionnaire.

Figure 3:
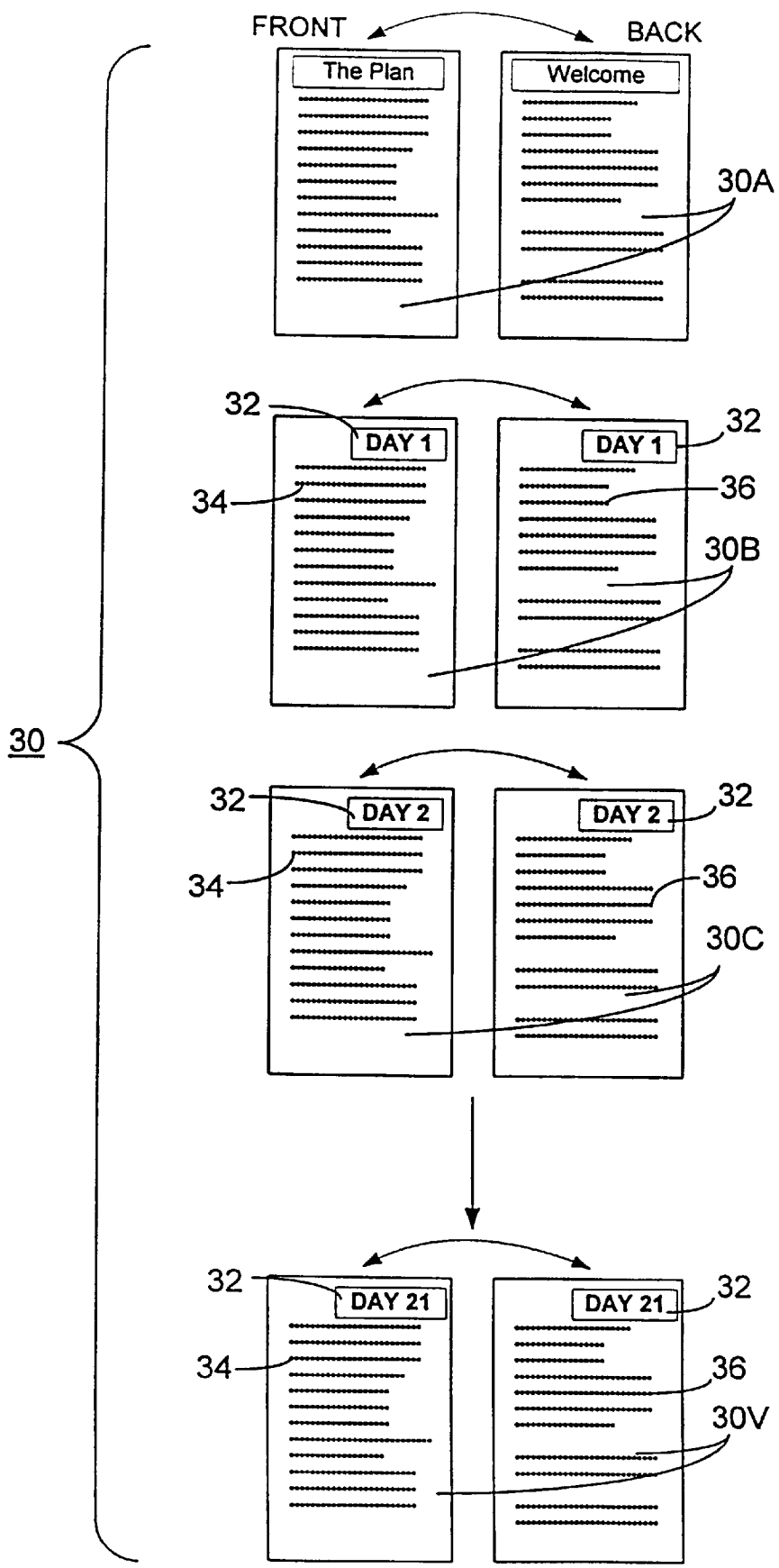
FIG. 3 is an illustration of plural cards or sheets which are produced in accordance with this invention to enable the person to achieve his/her goal, e.g., to quit smoking.

Irrespective of the manner in which the questions are presented to the individual and or the manner that his/her answers are provided back for use in the system, the answers form as what is identified as "questionnaire data" shown in block diagram in FIG. 3. It is this questionnaire data which the system 20 uses to develop the tailored plan for the individual. In particular, the system 20 includes a computer 24 into which the questionnaire data is input. That data may be entered into the computer 24 via keyboard entry, telephonic connection, or any other suitable means, e.g., voice recognition software, etc. The inputting of the personal information data into the computer 24 starts the "Personal Plan Generation Phase" of the subject invention.

In accordance with one preferred aspect of this invention, the computer 24 preferably makes use of "expert system" software to establish the algorithms for processing the questionnaire data into a smoking cessation plan specifically designed and developed for the individual. The plan produced by the system 20 is arranged to be communicated to the individual by means of the series of daily messages 30 in the form of coherent narrative instructions, divided into non-dated daily sections for the individual to follow. The messages are preferably in hard copy form, e.g., printed sheets or cards 30 (FIG. 1). The sheets or cards 30 may be communicated or delivered to the individual in any suitable way. For example, they may be printed out by a printer 26 associated with the system computer 24 and then mailed or otherwise delivered to the individual. If the individual has a computer system with a printer, the messages may be delivered electronically, e.g., via the Internet, e-mail, facsimile, etc., to the individual. While it is preferable that the messages ultimately be reduced to hard copy form (e.g., a series of cards or sheets, like those to be described later) the messages may be transient or stored electronically so that they only appear on the video monitor associated with the individual's computer 22.

In any case and in accordance with the preferred embodiment of this invention, each of the daily messages 30 includes coherent narrative instructions relevant to the particular day of the plan, that is a series of instructions for the "first" day, the "second" day, the "third" day, etc. Moreover, as can be seen in FIGS. 1 and 3, each of the daily messages 30 bears indicia 32 on it indicating the relative day of the plan. Thus, the first day of the plan is identified as "Day 1" and is the day that the individual chooses to start the plan. That day can be any calendar date chosen by the individual, i.e., the starting date of the plan is not predetermined or preestablished to be a particular day. Thus, each of the daily messages 30 is non-dated. By non-dated it is meant that each message does not have any calendar date thereon so that the individual is not tied to any particular calendar date for any particular activity as part of the plan. As mentioned earlier by associating a particular calendar date to a particular activity (e.g., June 9$^{th}$ being the "quit" or start day for the plan) if the user should miss that date, he or she may try to catch up to get back in synchronism, thereby detracting from the efficacy of the plan or dooming it to failure.

In FIG. 3 the daily sheets or cards 30 produced in accordance with this plan are illustrated in grossly simplified form in the interest of drawing simplicity. Thus, as can be seen the series of sheets/cards 30 include a first sheet or card 30A having a front side and a rear or back side. The next consecutive sheet or card is the "Day 1" sheet or card 30B. It too includes a front side and a back side. The next successive card is the "Day 2" card 30C which has a front side and a back side. In accordance with one exemplary embodiment the smoking cessation plan is of a duration of twenty-one days. Thus, the last of the daily cards or messages is identified as the "Day 21" card 30V. If desired, additional cards (not shown) may be provided in the form of "Maintenance Instruction" cards.

As can be seen in FIGS. 1, 3 and 5 the front side of each card bears indicia 32 indicating of the day of the plan. The front side also includes indicia 34 bearing the narrative instructions for the regimen of that day. On the reverse or back side of each sheet or card 30 there is indicia 36 bearing information which is relevant to the type of behavior at issue, but which is generalized and not particularly tailored for the individual. The narrative instructions 34 which appear on the front side of each of the cards/sheets 30 and which have been customized for the individual include a sufficient amount of material in coherent narrative form to provide substantial guidance for the individual to follow that day.

It is preferred that the individual be provided with a sheet or card for each day of the plan on the day for that card so that he/she is not be exposed to any of the cards or sheets for subsequent days of the plan in order to avoid overwhelming him/her with excessive information and distracting him/her with prematurely disclosed later stage instructions. To that end, if the cards or sheets are delivered electronically via the Internet, facsimile, e-mail, etc., they are preferably delivered one at a time, each day of the plan. If all the sheets or cards for the plan are delivered at one time, the individual is preferably instructed to only look and follow the instructions and information on the sheet or card 30 for that particular day of the plan.

Turning now to FIGS. 3 and 4, the details of two exemplary sheets or cards 30 will be described. Thus, as can be seen the first sheet or card 30 of the series, that is sheet or card 30A, is in the form of a "Personal Profile" card. To that end it includes a concise summarization of the personal profile of the individual on which the personal plan was based from the questionnaire answers. As can be seen in FIG. 4, the front side of the personal profile card 30A for an exemplary individual, "John Doe," indicates that Mr. Doe's age is 53, he is a male and there is one other smoker in his household. Mr. Doe smokes an average of 20 cigarettes a day. He has tried to quit three times. The longest period he has not smoked has been 3½ months. His last attempt to quit was in June 1979. He has tried nicotine replacement products, such as patch and gum. He smokes within 30 minutes of rising. He smokes for pleasure, stress relief and self-reward. He wants to quit for health concerns and pressure from his family. He fears gaining weight and lack of will-power as a barrier to his quitting. He believes his smoking habit is triggered as an after meal ritual or when he is driving or in a stressful situation or when he consumes alcohol. He is somewhat confident about his chances of success in quitting smoking.

As mentioned above all of the information appearing on the front side of the Personal Profile sheet or card 30A is derived from the answers to the questions presented to Mr. Doe during the Personal Data Collection Phase. The reverse side of the card 30A includes general information about smoking cessation for Mr. Doe's general guidance or information and has not been specifically tailored for him.

The next card or sheet 30 of the series of messages is the heretofore identified "Day 1" card or sheet 30B. This card or sheet is shown in detail in FIG. 5 and constitutes the first day of the plan. Thus, the indicia 32 appearing on the front side of the card 30B bears the indicia "Day 1." This day is Mr. Doe's "quit day." In addition the Day 1 card 30B bears detailed instructions in the form of indicia 34 on the front side of the card. These instructions are to be followed by John Doe on whatever day he decides should be "Day 1" or the "quit day" of his plan. In the exemplary embodiment in FIG. 5, the "Day 1" card of the plan focuses on Mr. Doe's specific concerns about gaining weight and lacking will-power. The reverse or back side of the "Day 1" card 30B includes a series of instructions which are generally applicable to those desiring to quit smoking, e.g., for Mr. Doe to get rid of all smoking materials. Specifically, Mr. Doe is advised to destroy all cigarettes and remove all ashtrays, lighters and matches from his home, workplace and car.

By following the recommendations appearing on the front and back side of the "Day 1" card, Mr. Doe will be on his way to breaking his habit of smoking. On the next successive day, Mr. Doe will read and follow the "Day 2" card 30B, and in particular its tailored instructions 34 and its generalized information 36 appearing on the front and back of the card, respectively. On the third day of the plan Mr. Doe will direct his attention to the "Day 3" card to follow the regimen presented thereby. This procedure is to be followed by Mr. Doe for each successive day of the plan through "Day 21," at which point Mr. Doe should have broken his habit of smoking. At this point Mr. Doe can be provided with detailed maintenance instructions. Those instructions can be in the form of additional cards or sheets (not shown) or may be messages delivered by some electronic communication means, such as facsimile, e-mail, etc. If appropriate, instructions can be provided by personal contact, a telephone conversation, regular mail, etc.

In accordance with another preferred aspect of this invention, a computer generated follow-up can be provided to Mr. Doe, via the Internet, e-mail, facsimile, personal contact, or some other means. The follow-up is provided to determine how well Mr. Doe has done in accomplishing his goal of quitting smoking. If any additional assistance is necessary it can be provided to him in any suitable manner.

As mentioned above the "Personal Profile" of the individual is established by his/her answers to the questionnaire, and serves as a basis for the development of the customized regimen or plan produced for that individual by the system of the subject invention. In some applications, it may be desirable to enable the individual to provide the system with updated personal information so that his/her personal profile may be modified or adjusted during the days making up the plan in order to more closely tailor the plan to him/her. The implementation of such modifications/adjustments to the plan can be readily accomplished in various ways. For example, if the system of the subject invention is connected to the Internet and a web-site is provided, the person may be given a personal identification number (PIN) to gain access to that web-site, where he/she could provide updated personal information about himself/herself. The system's computer in conjunction with the expert system software will then operate on that information to update the personal profile and generate succeeding messages based on the updated profile. These updated messages are preferably be provided back to the person immediately, e.g., while the person is still at the web-site. Alternatively, the modified or adjusted messages may be delivered in any other suitable manner or at any suitable time by any means, e.g., like those discussed earlier with respect to the unmodified messages.

The following constitutes one exemplary procedure in a smoking cessation program to provide a person, John Doe, with messages which are adjusted or modified in accordance with updated information provided by him/her to the system of this invention. During the course of the 21-day program, John Doe receives cards/sheets as discussed above and which reflect his initial personal profile (i.e., the personal profile developed in response to his answers to the questionnaire). However, using any suitable electronic communication media, e.g., the Internet, John Doe has the option of daily opportunities to edit his personal profile. Thus, each day he can access the system, e.g., visit and log onto the web-site, and respond to further questions designed specifically for someone of his profile at that specific point in time. Based on the John Doe's responses, the expert software of the system designs a set of instructions for the next 24 hours and prompts him to check-in tomorrow and "let us know how you are doing." If, for example, if it's the 11$^{th}$ day ("Day 11") of the plan and John Doe is having a particularly difficult time dealing with anger/stress and he provides that information to the system when he has logged into the web-site, the system will adjust the 12$^{th}$ day ("Day 12") message accordingly. Thus, the Day 12 message will include not only the standard instructions for that day, but also helpful hints on how John Doe can handle stressful situations without a cigarette.

As should be appreciated by those skilled in the art of health-related behavior modification techniques, the ability to modify or adjust a health-related behavior plan as it is being carried out (on-the-fly) is a powerful feature, since it mimics what would typically occur in a person-to-person intervention program. Another factor that can have critical importance to a successful change process is the amount and quality of external support provided to the individual. For example, a sensitive and informed support network can greatly enhance the likelihood that positive behavior change is initiated and, more importantly, sustained.

While there is a great deal of information that targets individuals seeking change, very little exists on how to be a support person. All to often, the process is approached intellectually, such as presenting logical information to the person in the hope he/she will see the wisdom of the information and simply change. This may be called the "do-the-right-thing" approach. While logical, it denies the psychological, sociological, and physiological complexity of lifestyles. Thus, using the "do-the-right-thing" approach by brow-beating an individual desiring to effect a change in his/her behavior with facts, logic, and emotional blackmail (e.g., a loved-one stating "if you really love me, you'll change") is likely to be counter-productive, since it often triggers reactions of guilt, anger, and fear in the individual. The need to escape from these feelings often leads the individual directly to the very health-related behavior which is attempted to be modified or ended (e.g., smoking, excessive drinking, drug abuse, sedentary lifestyle, etc.).

Taking the foregoing into account, the system and method of the subject invention may be implemented by encouraging and educating another person/persons with whom the individual wishing to change his/her health-related behavior has a close, personal relationship. This other person(s) is deemed to be a "lifestyle coach" and will have on-going access to the system 20, the plan or regimen developed for the individual, and to "coaching information." The coaching information is tailored to help the coach understand the chronological process of change and offer interactive opportunities to improve the quality of his/her coaching for the individual. To that end, in accordance with one preferred aspect the of this invention the system 20 is arranged to develop a tailored reference coaching plan which will correlate directly with the tailored program being used by the individual wishing to change his/her behavior. The tailored coaching plan can be developed through use of a questionnaire or any suitable means and is preferably provided to the coach in the form of daily messages, correlated to those provided to the individual undergoing the behavior-change process. For example, if John Doe, is in any day (e.g., "Day 4") of his smoking cessation program, his coach may receive a tailored message that deals specifically with the concerns associated with that day. These daily messages may be delivered to the coach in any suitable manner (e.g., through Internet access). Each message bears indicia indicating the day of the plan, e.g., "Day 4," blocks of generic textual information relating generally to the behavior in issue, as well as specific or tailored information for the coach to make use of in assisting John Doe to break the smoking habit. In fact, the system 20 is designed so that the coach can query the expert system software for additional tips, as well as respond to a series of questions designed to determine or measure how well he/she is responding to specific challenges in coaching the individual.

As discussed earlier the expert system software has within it the interest profile of the individual desiring to modify his/her health-related behavior (the profile having been developed by the system in response to the individual's answers to a questionnaire). Preferably, the interest profile of each coach will also be resident in the system and will have been developed by the expert system software in response to a questionnaire answered by the coach or from information gathered from the coach in some other manner.

The use of the profiles of both the individual undergoing the behavior modification and his/her coach enables the system 20 to provide the coach with messages which enable him/her to better support the individual's efforts. For example, to aid John Doe's coach in helping John Doe to stop smoking, a message his coach may receive on one day may read: "Because John Doe enjoys bowling, as do you, you may suggest that the two of you go to the local alley, bowl a couple of games, and enjoy your time together."

As mentioned earlier the system 20 is designed to also capture up-to-the-minute information from the individual undergoing the health-related behavior modification to modify his/her plan "on-the-fly." To further facilitate such plan modification(s), the system 20 is preferably arranged to advise the coach of any changes or modifications to the plan resulting from the daily input of the individual. These daily change notices are provided to the coach in the messages provided to him/her.

It must be reiterated at this juncture that the subject system and methodology has wide applicability, and thus is not limited to smoking cessation plans. Thus, it can be used to modify any undesirable behavior. Moreover, it can be used to establish a plan for maintaining a desired behavior, e.g., it can be used to help a person who has already quit smoking to maintain that behavior, to aid a person who has lost weight to keep the weight off, etc. In fact, the subject system and method can be used in any application calling for habitual behavior modification and/or maintenance, whether or not health related.

Without further elaboration the foregoing will so fully illustrate my invention that others may, by applying current or future knowledge, adopt the same for use under various conditions of service.

What is claimed is:

1. A method of providing perceptible information to a person to aid the person to alter an undesirable health-related habitual behavior or to maintain a desirable health-related behavior by following a customized regimen to commence on a day to be selected by the person, said method comprising the steps of:

(A) collecting data from the person based on the person's answers to a series of questions;

(B) utilizing said data in a computer to process said data and provide a series of specific customized behavioral change messages as part of a customized regimen to aid the person to alter the undesirable health-related behavior or maintain the desirable health-related behavior, said messages being provided in a daily sequence measured relative to said selected day;

(C) providing said customized messages in visually perceptible form to the person in sequence on a daily basis, each of said customized messages including respective numerical indicia representing the number of days from the selected day to the day of said customized message; and (D) arranging said customized messages so that each is seen on the day associated therewith to deter the person from seeing more than a single day's message at a time.

2. The method of claim 1 wherein said customized messages are provided in printed form.

3. The method of claim 2 wherein each of said customized messages is printed on its own sheet.

4. The method of claim 3 wherein each of said sheets includes a first side with said customized message thereon and a second side bearing indicia containing information generally relevant to undesirable or desirable health-related behavior.

5. The method of claim 1 wherein the undesirable health-related behavior constitutes smoking.

6. The method of claim 1 wherein each of said customized messages is delivered to the person via an electronic communication medium.

7. The method of claim 6 wherein said electronic communication medium is selected from the group consisting of facsimile, e-mail, and the Internet.

8. The method of claim 7 wherein each of said series of customized messages is delivered daily to the person by said electronic communication medium.

9. The method of claim 7 additionally comprising the step of printing out said customized messages from said electronic communication medium.

10. The method of claim 8 wherein each of said customized messages is printed on its own sheet.

11. The method of claim 1 wherein said series of questions is communicated to the person by means of one or more of the group consisting of the Internet, e-mail, facsimile, a printed questionnaire, a personal computer program, a personal interview, or a telephonic interview.

12. The method of claim 1 wherein said data is communicated to said computer by means of one or more of the group consisting of magnetic media, optical media, a computer keyboard, a telephone touch-pad, and voice recognition software.

13. The method of claim 11 wherein said data is communicated to said computer by means of one or more of the group consisting of magnetic media, optical media, a computer keyboard, a telephone touch-pad, and voice recognition software.

14. The method of claim 1 wherein said method comprises providing said computer with expert system software to produce said customized messages in the form of coherent narrative instructions.

15. The method of claim I wherein said customized messages are established based on the answers of the person to a series of questions prior to the start of the regimen, and wherein said method additionally comprises modifying some of the messages of the regimen during the regimen and based upon further information provided by the person.

16. The method of claim 15 wherein the answers to said questions establish a personal profile for the person, and wherein the further information provided by the person updates the personal profile.

17. The method of claim 15 wherein said further information is provided by the person via electronic communication means.

18. The method of claim 16 wherein said further information is provided by the person via electronic communication means.

19. The method of claim 18 wherein the person is given a personal identification number to gain access to said system to update the person's personal profile.

20. The method of claim 18 wherein said electronic communication means comprises the Internet.

21. The method of claim 1 wherein support messages are communicated to a support person to aid the person wishing to alter an undesirable health-related habitual behavior or to maintain a desirable health-related behavior.

22. The method of claim 21 wherein said support messages are developed by said computer based on the answers of the person to a series of questions provided to said support person.

23. The method of claim 22 wherein said messages are communicated to said support person in a similar manner to the manner in which said messages are communicated to said person wishing to alter an undesirable health-related habitual behavior or to maintain a desirable health-related behavior.

24. A system to help a person to alter an undesirable habitual health-related behavior or to maintain a desirable health-related behavior by following a calculated regimen to commence on a day to be selected by the person, said system comprising a computer and a series of customized visually perceptible messages establishing a customized regimen to aid the person to alter the undesirable health-related behavior or to maintain the desirable health-related behavior, said computer being arranged for receipt of data collected from the person based on the person's answers to a series of questions to process said data to provide said customized messages, said series of customized messages being in a daily sequence measured relative to said selected day, each of said messages being arranged to be visually perceived by the person in sequence on a daily basis and including respective numerical indicia representing the number of days from the selected day to the day of said message, each of said series of customized messages being arranged so that each is seen on the day associated therewith to deter the person from seeing more than a single day's message at a time.

25. The system of claim 24 wherein said messages are in printed form.

26. The system of claim 25 wherein each of said messages is on a respective sheet.

27. The system of claim 26 wherein each of said sheets includes a first side with said customized message thereon and a second side bearing indicia containing information generally relevant to the desirable and undesirable health-related behavior.

28. The system of claim 24 additionally comprising electronic communication means for producing and carrying each of said messages in electronic form to a printer for printing each of said messages into a hard copy.

29. The system of claim 24 wherein said electronic communication means is selected from the group consisting of facsimile, e-mail, and the Internet.

30. The system of claim 24 additionally comprising expert system software associated with said computer to produce said customized messages in the form of coherent narrative instructions.

* * * * *